United States Patent [19]
Blackburn et al.

[11] Patent Number: 5,753,614
[45] Date of Patent: *May 19, 1998

[54] NISIN COMPOSITIONS FOR USE AS ENHANCED, BROAD RANGE BACTERICIDES

[75] Inventors: Peter Blackburn; June Polak; Sara-Ann Gusik; Stephen D. Rubino, all of New York, N.Y.

[73] Assignee: AMBI Inc., Tarrytown, N.Y.

[*] Notice: The term of this patent shall not extend beyond the expiration date of Pat. No. 5,691,301.

[21] Appl. No.: 470,929

[22] Filed: Jun. 6, 1995

Related U.S. Application Data

[60] Continuation of Ser. No. 149,439, Nov. 9, 1993, Pat. No. 5,691,301, which is a division of Ser. No. 870,803, Apr. 17, 1992, Pat. No. 5,260,271, which is a continuation of Ser. No. 317,626, Mar. 1, 1989, abandoned, which is a continuation-in-part of Ser. No. 209,861, Jun. 22, 1988, abandoned.

[51] Int. Cl.$^6$ ............................................. A61K 38/16
[52] U.S. Cl. ....................................... 514/2; 514/12
[58] Field of Search ............................................. 514/2, 12

[56] References Cited

U.S. PATENT DOCUMENTS

| | | | |
|---|---|---|---|
| 2,744,827 | 5/1956 | Mattick et al. | 99/162 |
| 3,579,354 | 5/1971 | Kasik et al. | 99/116 |
| 3,867,521 | 2/1975 | Nickel et al. | 424/37 |
| 3,899,594 | 8/1975 | Nickerson et al. | 426/9 |
| 3,988,307 | 10/1976 | Gross | 260/112.5 |
| 4,158,607 | 6/1979 | Kalinowksi et al. | 195/62 |
| 4,318,928 | 3/1982 | Sing | 426/38 |
| 4,474,751 | 10/1984 | Haslam et al. | 424/78 |
| 4,477,471 | 10/1984 | Gonzalez | 426/43 |
| 4,485,029 | 11/1984 | Kato et al. | 252/106 |
| 4,584,199 | 4/1986 | Taylor | 426/36 |
| 4,597,972 | 7/1986 | Taylor | 426/36 |
| 4,684,643 | 8/1987 | Buddenham et al. | 514/204 |
| 4,716,115 | 12/1987 | Gonzalez et al. | 435/68 |
| 4,832,952 | 5/1989 | Heish et al. | 424/400 |
| 4,980,163 | 12/1990 | Blackburn et al. | 430/94.63 |
| 5,217,950 | 6/1993 | Blackburn et al. | 514/2 |
| 5,260,271 | 11/1993 | Blackburn et al. | 514/2 |
| 5,304,540 | 4/1994 | Blackburn et al. | 514/2 |

FOREIGN PATENT DOCUMENTS

| | | |
|---|---|---|
| 6068616 | 6/1981 | Japan . |
| 0738655 | 10/1955 | United Kingdom . |

OTHER PUBLICATIONS

Chemical Abstracts, vol. 77 (1972), p. 14; vol. 82 (1975) p. 94, vol. 86 (1977) p. 58; vol. 89 (1978) pp. v64–65.
Hurst, *Advances in Applied Microbiology* 27: 85–123 (1981).
Morris et al., *J. Biol. Chem*, vol. 259, pp. 13590–13594 (1984).
Ruhr et al., *Antimicrob.Agents Chemother*, vol. 27, pp. 841–845 (1985).
Tsai et al, *Appl. Environ. Microbiol*, vol. 53, pp. 352–357 (1987).
J. Roger Hart, "Chelating Agents As Preservative Potentiators", W.R. Grace & Co., 323–337 (1984).
"A Natural Preservative" *Food Eng. Int'l.*, May 1987, pp. 37–38.
Zygmunt et al. "Lysostaphin: Model for a Specific Enzymatic Approach to Infections Disease", *Progress in Drug Research* 16, 1972, pp. 309–333.
Claypool et al. *Journal of Dairy Science* 49, 314–315 (1966).
Cowell et al., *J. Appl. Bact.* 34 (4), 787–791 (1971).
Johnson et al., *J Appl. Bact.* 45 (1978), pp. 99–109.
"The Food Preservative Nisaplin –Technical Data".
*Federal Register*, vol. 47, No. 101, May 25, 1982.
Kordel et al., *FEB* 06784, vol. 244, No. 1, Feb. 1989 pp. 99–102.
Weber et al., "Quaternary Ammonium Compounds," *Soap & Sanitary Chemicals*, Sep. 1948, pp. 137–142.
J Roger Hart, "Chelating Agents a Preservative Potentrators," W R Grace & Co. 1984 pp. 323–337.
"Focus on Nisin", Ford Manufacture, Mar. 1987, pp. 63–64.
Hurst, Adv. in Applied Microbiol, vol. 27, pp. 85–123, 1981.

*Primary Examiner*—Chhaya D. Sayala
*Attorney, Agent, or Firm*—White & Case L.L.P.

[57] ABSTRACT

Bacteriocin compositions comprising lanthionine containing bacteriocins and non-bactericidal agents. When the bacteriocin compositions are combined with a suitable carrier with each component present in sufficient quantities such that the composition is effective against Gram negative bacteria in addition to Gram positive bacteria, they become enhanced, rapid acting, broad range bactericides suitable for a variety of applications.

14 Claims, No Drawings

NISIN COMPOSITIONS FOR USE AS ENHANCED, BROAD RANGE BACTERICIDES

This application is a continuation of application Ser. No. 08/149,439, filed on Nov. 9, 1993, U.S. Pat. No. 5,691,301 which is a divisional application of Ser. No. 07/870,803, filed on Apr. 17, 1992 and Issued on Nov. 3, 1993 as U.S. Pat. No. 5,260,271, which is a continuation of application Ser. No. 07/317,626, filed on Mar. 1, 1989 (abandoned), which is a continuation-in-part of application Ser. No. 07/209,861, filed on Jun. 22, 1988 (abandoned).

BACKGROUND OF THE INVENTION

Nisin is a polypeptide with antimicrobial properties which is produced in nature by various strains of the bacterium *Streptococcus lactis*. It is a known food preservative which inhibits the outgrowth of spores of certain species of Gram positive Bacilli.

Although sometimes mistakenly and imprecisely referred to as an antibiotic, nisin is more correctly classified as a bacteriocin, i.e. a proteinaceous substance produced by bacteria and which has antibacterial activity only towards species closely related to the species of its origin. Nisin is a naturally-occurring preservative found in low concentration in milk and cheese, and is believed to be completely non-toxic and non-allergenic to humans.

Nisin has recently been recognized as safe by the FDA as a direct food ingredient in pasteurized cheese spread, pasteurized processed cheese spread, and pasteurized or pasteurized processed cheese spread with fruits, vegetables, or meats. Furthermore, since it is a polypeptide, any nisin residues remaining in foods are quickly digested.

A summary of nisin's properties appears in Hurst, A., *Advances in Applied Microbiology* 27:85-123 (1981). This publication describes what is generally known about nisin. Nisin, produced by *Streptococcus lactis*, is available commercially as an impure preparation, Nisaplin™, from Aplin & Barrett Ltd., Dorset, England and can be obtained by isolating naturally-occurring nisin from cultures of *Streptococcus lactis* and then concentrating the nisin according to known methods. There are also reported methods for producing nisin using altered strains of Streptococcus. See Gonzalez et al., U.S. Pat. No. 4,716,115, issued Dec. 29, 1987. It should also be possible to produce nisin by recombinant DNA technology.

Nisin has been applied effectively as a preservative in dairy products, such as processed cheese, cream and milk. The use of nisin in processed cheese products has been the subject of recent patents. See U.S. Pat. Nos. 4,584,199 and 4,597,972. The use of nisin to inhibit the growth of certain Gram positive bacteria has been well documented. However, its complete success and acceptance as a food preservative has heretofore been hampered by the belief that nisin was ineffective against Gram negative and many Gram positive bacteria. Gram negative bacteria are almost always present in conjunction with Gram positive bacteria and are a major source of food spoilage and contamination. See Taylor, U.S. Pat. No. 5,584,199, issued Apr. 22, 1986 and Taylor, U.S. Pat. No. 4,597,972, issued Jul. 1, 1986; Tsai and Sandine, "Conjugal Transfer of Nisin Plasmid Genes from *Streptococus Lactis* 7962 to *Leuconostoc Dextranicum* 181, *Applied and Environmental Microbiology*, February 1987, p. 352; "A Natural Preservative," *Food Engineering Int'l*, May 1987, pp. 37–38; "Focus on Nisin," *Food Manufacture*, March 1987, p. 63.

SUMMARY OF THE INVENTION

It has now been found that contrary to prior teaching, compositions comprising nisin, in combination with various non-bactericidal agents have enhanced, broad range bactericidal activity against Gram negative bacteria as well as enhanced activity against a broader range of Gram positive bacteria than nisin alone. The enhanced bactericidal activity against Gram positive bacteria occurs in a pH range broader than previously taught. The invention provides bacteriocin compositions of nisin or other, lanthionine containing bacteriocins, in combination with various non-bactericidal agents for example chelating agents or surfactants. The invention further provides the compositions dissolved or suspended in a suitable carrier to yield enhanced broad range bactericides.

DETAILED DESCRIPTION OF THE INVENTION

Specifically, it has been found that a solution of about 0.1 µg/ml to 300 µg/ml of nisin in the presence of about 0.1 mM to 20 mM of a chelating agent, for example EDTA, virtually eliminates the growth of Gram negative bacteria such as *Salmonella typhimurium*, *Escherichia coli*, *Pseudomonas aeruginosa*, *Bacterioides gingivalis*, *Actinobacillus actinomycetescomitans*, and *Klebsiella pneumoniae* and is more active towards Gram positive bacteria such as *Staphylococcus aureus*, *Streptococcus mutans*, *Listeria monocytogenes Streptococcus agalactiae* and Coryneform bacteria than nisin alone. Although the enhancement of nisin activity by chelator was concentration dependent, contrary to expectations, concentrations of EDTA in excess of 20 mM were inhibitory to the bactericidal activity of nisin. However, in the presence of a proteinaceous carrier, and polyvalent polymers such as serum albumin, collagen, gelatin, casein and keratin, the inhibition of nisin by concentrations of EDTA above 20 mM was significantly reduced, thereby extending the useful range of EDTA enhancement of nisin.

It has also been found that a solution of about 0.1 µg/ml to 300 µg/ml nisin and about 0.1 mM to 20 mM of a chelating agent will further enhance the effectiveness of nisin against Gram negative and Gram positive bacteria in the presence of about 0.01% to 1.0% of surfactant. Additionally, it has been found that, in the presence of surfactant alone, nisin has enhanced activity against Gram positive bacteria.

In the present invention, suitable chelating agents include, but are not limited to, EDTA, CaEDTA, CaNa$_2$EDTA, and other alkyldiamine tetraacetates, EGTA and citrate. Surfactants, valuable as cleansing agents, suitable for combination with nisin, with or without EDTA, include, but are not limited to, the nonionic surfactants Tweens, Tritons, and glycerides, ionic surfactants such as fatty acids, quaternary compounds, anionic surfactants such as sodium dodecyl sulphate and amphoteric surfactants such as cocamidopropyl betaine and emulsifiers.

Since Gram positive and Gram negative bacteria are almost always found together in foods, the effectiveness of the nisin compositions towards Gram negative bacteria such as *Salmonella typhimurium*, *Escherichia Coli*, *Klebsiella pneumoniae*, *Pseudomonas aeruginosa*, *Bacterioides gingivalis*, *Actinobacillus actinomycetescomitans*, and other Gram negative pathogens and Gram positive bacteria will be of great use. The bactericides are particularly suited for the control and prevention of contamination of raw ingredients, processed foods and beverages by bacterial pathogens and other microbial spoilage organisms. Potential food related uses include treatment of meats, especially poultry, eggs, cheese and fish and treatment of food packaging and handling equipment. Further uses include as food preservative, such as in processed cheese, cream, milk, dairy products and in cleaning poultry, fish, meats, vegetables, and dairy and food processing equipment. The use of the nisin compositions should not be limited to food related uses and the nisin compositions should be useful in any situation in which there is a need or desire to eliminate Gram negative and Gram positive bacteria.

The compositions can be dissolved in a suitable carrier for example an aqueous solvent or buffer or suspended in any suitable liquid, colloidal or polymeric matrix to create bactericides. The compositions or bactericides can be incorporated into ointments or coatings for medicinal uses such as the treatment of infections, wound dressings or surgical implants and as a broad spectrum disinfectant for skin or oral rinses, disinfectant scrubs, wipes or lotions. The bactericides can be used for cleaning medical instruments, in pre-operative surgical scrubs and the like. The bactericides are particularly useful in circumstances where environmental disinfection is desired but where chemical germicidals are precluded because of the risks of corrosive or otherwise toxic residues.

Unlike the activity of most broad spectrum germicidals which is compromised by the presence of complex organic matter, the compositions of the present invention are effective as bactericides in the presence of organic matter, such as milk or serum.

Nisin was known to optimally inhibit the growth of a few closely related Gram positive bacteria, particularly certain Gram positive spore forming bacilli at pH 5.0. The bactericidal activity of nisin in solution with a chelating agent was surprisingly rapid and greatly enhanced towards a broad range of Gram positive bacteria at pH values greater than pH 5.0, and, moreover, was activated towards Gram negative bacteria at both acidic and basic pH, preferably in the range pH 5.0 to 8.0. This unexpectedly rapid and broad-ranged bactericidal activity of chelator-activated nisin makes it suitable for use as, among other things, a disinfectant.

Nisin belongs to the class of peptide bacteriocins containing lanthionine. Also included among that class are subtilin, epidermin, cinnamycin, duramycin, ancovenin and Pep 5. These bacteriocin peptides are each produced by different microorganisms. However, subtilin obtained from certain cultures of Bacillus subtilis, and epidermin obtained from certain cultures of Staphylococcus epidermidis, have been found to have molecular structures very similar to that of nisin (see Hurst, pp. 85–86, and Schnell et al., Nature, 333:276–278). It is therefore believed that because of the molecular similarities, other lanthionine containing peptide bacteriocins will be equally as effective as nisin in combination with chelating agents and non-ionic surfactants in eliminating Gram negative and Gram positive bacterial contaminations.

The effectiveness of the nisin, and by extension other lanthionine containing peptide bacteriocin, compositions as bactericides against Gram negative bacteria is surprising, since the prior art generally teaches away from this activity of nisin. The enhanced activity of nisin against Gram positive bacteria in the presence of EDTA at a pH greater than 5.0 is unexpected since it was previously believed that nisin activity is optimal at pH 5.0. Furthermore, the discovery of such effectiveness of the nisin and lanthionine containing peptide bacteriocin compositions as bactericides fulfills-a long-felt need in the science of food preservation, which has suffered from the absence of an acceptable, natural, non-toxic agent effective against a broad range of bacteria.

In order to demonstrate the superior and unexpected rapid activity of the composition containing nisin, EDTA and/or various surfactants against both Gram negative and Gram positive bacteria, a number of experiments were conducted with the bactericides. These experiments are meant as illustration and are not intended to limit this invention.

It is to be expected that other, lanthionine containing peptide bacteriocins would be effective substitutes for nisin and that chelating agents other than EDTA will be effective substitutes for EDTA.

All tests in the following examples were performed at 37° C. The efficacy of the enhanced broad range bactericides was determined by assaying bactericidal activity as measured by the percent bacterial survival after treatment with the bactericide. Generally, after incubation of a $10^7$ cell per ml suspension of target species with the novel bactericide for specified lengths of time, bacteria were collected by centrifugation for 2 minutes. The bacterial pellet was washed free of the bactericide with a rescue buffer, termed herein Phage buffer (50 mM Tris-HCl buffer pH 7.8, 1 mM $MgSO_4$, 4 mM $CaCl_2$, 0.1M Nacl, and 0.1% gelatin), resuspended and serially diluted into Phage buffer, and 100 µl of the suspended bacteria were spread on nutrient agar plates. Surviving bacteria were determined by scoring colony forming units (CFU) after incubation for 24–48 hours at 37° C.

An effective bactericide according to this invention is one which allows less than 0.1% of the initial viable count of the bacteria to survive.

EXAMPLE 1

Activity of Nisin and a Chelating Agent Against Gram Negative Bacteria (S. typhimurium)

As shown in Table 1, two tests were conducted in 20 mM Tris, pH 8.0 at 37° C. to show the effect of the bactericide containing nisin and the chelating agent EDTA alone. Test #1, a control, was conducted without EDTA and shows the effect of nisin alone toward the Gram negative bacterium S. typhimurium. The increased concentrations of nisin do exhibit some activity, but even the activity of the higher concentrations in the absence of EDTA, 1.6% survival at 100 µg/ml nisin, is wholly inadequate for a food preservative. The level of bactericidal activity obtained from nisin and EDTA is significant.

TABLE 1

| Test # | Initial Viable Bacteria Count | EDTA (mM) | Nisin (µg/ml) | | | | | |
|---|---|---|---|---|---|---|---|---|
| | | | 0 | 10 | 30 | 50 | 100 | 300 |
| | | | Percentage S. typhimurium Survival at 3 hours | | | | | |
| 1 | $3.0 \times 10^6$ | 0 | 100 | 51.3 | — | 7.0 | 1.6 | — |
| 2 | $5.7 \times 10^6$ | 20 | 2.5 | — | $10^{-3}$ | — | $<10^{-4}$ | $<10^{-4}$ |

Test #2 (Table 1), conducted using nisin plus 20 mM EDTA, demonstrates the surprising activity of the nisin composition in eliminating the target Gram negative bacteria.

Table 1 shows that in test #2 at a concentration of 20 mM EDTA and 30 µg/ml of nisin, the bactericide has a marked bactericidal activity towards S. typhimurium, while at nisin concentrations of 100 µg/ml and greater, the nisin and EDTA bactericide virtually eliminates the bacteria (percentage survival less than $10^{-4}$ which indicates no surviving bacteria in the assay). Thus, the combination of EDTA and nisin demonstrates a synergistic activity of greater than 1000 times that of nisin alone.

EXAMPLE 2

Activity of Nisin, a Chelating Agent and a Surfactant Against Gram Negative Bacteria (S. typhimurium)

Four tests (Table 2) were conducted to determine the effect on S. typhimurium of the bactericide containing nisin and both EDTA and the surfactant Triton X-100 in 20 mM Tris, pH 8.0 at 37°. The control (Test #1) is identical to the control of Example 1 (Table 1).

TABLE 2

| Test # | Initial Viable Bacteria Count | EDTA (mM) | Triton X-100 (%) | Nisin (µg/ml) | | | | | |
|---|---|---|---|---|---|---|---|---|---|
| | | | | 0 | 10 | 30 | 50 | 100 | 300 |
| | | | | Percentage S. typhimurium Survival at 3 hours | | | | | |
| 1 | $3.0 \times 10^6$ | 0 | 0 | 100 | 51.3 | — | 7.0 | 1.6 | — |
| 2 | $3.0 \times 10^6$ | 0 | 1.0 | 37.4 | 93.0 | — | 64.0 | 47.0 | — |
| 3 | $5.7 \times 10^6$ | 20 | 0.1 | 0.03 | — | $<10^{-3}$ | — | — | — |
| 4 | $5.7 \times 10^6$ | 20 | 1.0 | $<10^{-4}$ | — | $<10^{-4}$ | — | $<10^{-4}$ | $<10^{-4}$ |

Test #2 (Table 2) was conducted using nisin and 1.0% Triton X-100, but without EDTA. The presence of the detergent alone inhibits the activity of the nisin towards the Gram negative bacteria and nisin was ineffective. However, in tests #3 and #4 (Table 2), which represent the invention, the presence of 20 mM EDTA in combination with Triton X-100 is a bactericide which markedly increases the bactericidal activity of nisin towards S. typhimurium. Indeed the combination of Triton X-100 with EDTA but without nisin was effective, although to a lesser degree than in the presence of nisin. While in both tests #3 and #4 (Table 2) the nisin combinations were very effective, the concentration of 1.0% Triton X-100 (test #4, Table 2) was most effective.

The presence of the non-ionic surfactant, Triton X-100, in combination with EDTA, enhances the activity of nisin toward Gram negative bacteria even more than the bactericide containing nisin and EDTA alone (Example 1).

EXAMPLE 3

Activity of Nisin, a Chelating Agent and a Surfactant Against Gram Negative Bacteria (S. typhimurium)

Table 3 shows the enhanced activity toward S. typhimurium of the bactericide containing nisin, 20 mM of the chelating agent EDTA and the non-ionic surfactant Tween 20 in 20 mM Tris, pH 8.0 at 37° C. As with Triton X-100 (Example 2) the combination of nisin and EDTA with (1%) of Tween 20 is most effective.

TABLE 3

| Test # | Initial Viable Bacteria Count | EDTA (mM) | Tween20 (%) | Nisin (µg/ml) | | | | | |
|---|---|---|---|---|---|---|---|---|---|
| | | | | 0 | 10 | 30 | 50 | 100 | 300 |
| | | | | Percentage S. typhimurium Survival at 3 hours | | | | | |
| 1 | $3.0 \times 10^6$ | 0 | 0 | 100 | 51.3 | — | 7.0 | 1.6 | — |
| 2 | $5.7 \times 10^6$ | 20 | 0 | 2.5 | — | $<10^{-3}$ | — | $<10^{-4}$ | $<10^{-4}$ |
| 3 | $4.3 \times 10^6$ | 20 | 1.0 | $<10^{-2}$ | — | $<10^{-4}$ | — | $<10^{-4}$ | $<10^{-4}$ |

EXAMPLE 4

Activity of Nisin, a Chelating Agent and a Surfactant Against Gram Negative Bacteria (Escherichia coli)

The effect of the bactericide containing nisin and EDTA towards the Gram negative bacteria E. coli was demonstrated, as shown in Table 4.

TABLE 4

| Test # | Initial Viable Bacteria Count | EDTA (mM) | Triton X-100 (%) | Nisin (µg/ml) | | | |
|---|---|---|---|---|---|---|---|
| | | | | 0 | 30 | 100 | 300 |
| | | | | Percentage E. coli Survival at 2 hours | | | |
| 1 | $1.0 \times 10^7$ | 0 | 0 | 100 | 27 | 25 | 8.5 |
| 2 | $1.0 \times 10^7$ | 20 | 0 | 14.5 | 0.86 | 0.01 | 0.001 |
| 3 | $1.0 \times 10^7$ | 0 | 1.0 | 100 | — | 30 | — |
| 4 | $1.0 \times 10^7$ | 20 | 1.0 | 1.2 | 0.8 | 0.05 | $<10^{-4}$ |

The tests, with and without EDTA, were performed in 20 mM Tris buffer solution, pH 8.0 at 37° C., with an initial viable count of $1 \times 10^7$ E. coli cells/ml. The effects of the bactericide were measured as a function of percentage bacteria survival after 2 hours.

In test #1, (control, Table 4) without EDTA, nisin exhibited little meaningful activity toward the elimination of E. coli. In test #2 (Table 4), however, where 20 mM EDTA was present, the bactericidal composition exhibited substantial activity towards the E. coli bacteria. The activity increased in effectiveness as the concentration of nisin was increased. The combination of nisin with EDTA as a bactericide demonstrates a 1000 fold synergistic increase in effectiveness towards E. coli. In tests #3 and #4 (Table 4), it can be seen that Triton X-100 has no significant bactericidal activity towards E. coli. In fact, Triton X-100 appears to inhibit nisin activity towards Gram negative bacteria as was found with *S. typhimurium* (Table 2). However, the overall enhancement of nisin by EDTA substantially reverses the inhibitory effects of Triton X-100 as seen in Tables 2 and 4.

It thus appears that the bactericide containing nisin and a chelating agent, such as EDTA, is an effective food preservative towards various types of Gram negative bacteria even in the presence of surfactants.

EXAMPLE 5

Activity of Nisin and a Chelating Agent Against Gram Negative Bacteria (*Klebsiella pneumoniae*)

The effect of the bactericide containing nisin and EDTA alone towards the Gram negative bacteria *K. pneumoniae* was demonstrated, as shown in Table 5.

TABLE 5

| Test | Initial Viable Bacteria Count | EDTA (mM) | Triton X-100 (%) | Nisin µg/ml | | | |
|---|---|---|---|---|---|---|---|
| | | | | 0 | 30 | 100 | 300 |
| | | | | % Survival at 2 hours | | | |
| 1 | $10^7$ | 0 | 0 | 100 | — | 50 | 38 |
| 2 | $10^7$ | 20 | 0 | 22 | 0.5 | 1.1 | 0.085 |

The two tests, one with and one without EDTA (control), were performed in 20 mM Tris buffer, pH 8.0 at 37° C. with an initial viable count of $10^7$ cells/ml of *K. pneumoniae*. The effect was measured as a function of percentage bacterial survival after 2 hours.

In test #1, (control, Table 5) without EDTA, nisin exhibited little meaningful bactericidal activity toward *K. pneumoniae*. In test #2 (Table 5), however, where 20 mM EDTA was present, the bactericide exhibited substantial activity towards *K. pneumoniae*. The activity increased in effectiveness as the concentration of nisin was increased.

EXAMPLE 6

Nisin Activity Against Gram Negative Bacteria (*Salmonella typhimurium*) is Dependent on Chelator Concentration The data in Table 6 demonstrate that the enhanced activation of nisin towards Gram negative bacteria (*S. typhimurium*) is dependent on the concentration of EDTA in either 50 mM sodium acetate, pH 5.0, or 20 mM Tris, pH 8.0 at 37° C.

TABLE 6

| Test # | pH | Initial Viable Bacterial Count | Nisin µg/ml | EDTA (mM) | | | | | |
|---|---|---|---|---|---|---|---|---|---|
| | | | | 0 | 0.2 | 2.0 | 10 | 50 | 100 |
| | | | | % Survival at 2 hours | | | | | |
| 1 | 5.0 | $3 \times 10^6$ | 0 | 100 | — | 38.7 | 15.2 | 3.5 | — |
| 2 | 5.0 | $3 \times 10^6$ | 100 | 0.6 | $10^{-4}$ | $10^{-4}$ | 0.004 | 0.02 | — |
| 3 | 8.0 | $5 \times 10^6$ | 0 | 100 | — | 8.7 | 14 | 11.4 | 45 |
| 4 | 8.0 | $5 \times 10^6$ | 100 | 4 | $10^{-4}$ | $10^{-4}$ | $10^{-4}$ | 0.6 | 30 |

In tests #1 and #3, (controls, Table 6) using EDTA concentrations up to 100 mM without nisin exhibited little meaningful activity towards *S. typhimurium* at either pH 5.0 (#1) or pH 8.0 (#3). In tests #2 and #4 (Table 6), however, where 100 µg/ml nisin was present in combination with EDTA, the bactericides exhibited substantial activity towards *S. typhimurium*. The activity of the bactericides was similar at both acidic pH (5.0) and basic pH (8.0), despite the fact that the activity of nisin alone towards Gram positive bacteria is optimal at pH 5.0.

The enhancement of nisin by EDTA was concentration dependent, being optimal in the range 0.2 mM to 10 mM at pH values 5.0 and 8.0. Surprisingly, at concentrations greater than 10 mM EDTA, the enhancement of nisin by EDTA becomes reduced; the reduction of activation is significantly greater at pH 8.0 than at pH 5.0.

EXAMPLE 7

Nisin and a Chelating Agent Against Gram Negative Bacteria (*S. typhimurium*)

The enhancement of the activity of nisin by EDTA towards Gram negative bacteria in the presence of biological tissue was demonstrated with *S. typhimurium* on chicken muscle, and is shown in Table 7.

TABLE 7

| Test # | pH | Nisin ug/ml | EDTA (mM) | | | | | | | | |
|---|---|---|---|---|---|---|---|---|---|---|---|
| | | | 0 | 0.1 | 0.3 | 1 | 3 | 10 | 20 | 30 | 100 |
| | | | % Survival[a] at 2 hours | | | | | | | | |
| 1 | 5.0 | 0 | 11.8 | — | — | — | — | 6.4 | — | — | — |
| 2 | 5.0 | 300 | 0.1 | 0.2 | 0.05 | 0.01 | 0.003 | 0.016 | 0.03 | 0.02 | 0.07 |
| 3 | 8.0 | 0 | 100 | — | — | — | — | 5.2 | — | — | — |
| 4 | 8.0 | 300 | 7.5 | 0.1 | 0.02 | 0.02 | 0.09 | 0.47 | 0.5 | — | 2.2 |
| 5 | 8.0 | 300[b] | 0.02 | 0.09 | 0.0002 | <10$^{-4}$ | 0.0004 | 0.003 | — | 0.03 | 0.09 |

[a]Unadhered cells
[b]Contains 1% Bovine serum albumin (BSA)

Incubations were performed in either 50 mM sodium acetate, pH 5.0, or 20 mM Tris, pH 8.0 at 37° C.

Cubes of chicken muscle were cleansed with sodium hypochlorite and povidone iodine prior to use. To inoculate the tissue, the cubes of chicken muscle were dipped into a $10^8$ cells/ml suspension of S. typhimurium in 20 mM Tris HCl, pH 8.0. Excess moisture was removed from dipped cubes by tapping. The chicken samples were placed into sufficient buffer containing the nisin composition to cover the tissue and incubated for 2 hours at 37° C. after which the tissue was removed to sufficient Phage buffer to cover the tissue. The bacteria remaining in the test solution were collected by centrifugation, washed with Phage buffer, and combined with bacteria washed from the tissue by Phage buffer. The combined samples (termed "unadhered" cells) were serially diluted and 100 μl aliquots were plated for determination of surviving bacteria.

In tests #1 and #3 (Table 7), in the absence of nisin at either pH 5 or pH 8, EDTA alone has no significant effect on the survival of S. typhimurium. In tests #2 and #4 (Table 7), however, where 300 μg/ml nisin was present, the bactericides exhibited substantial activity towards S. typhimurium on chicken muscle at both pH 5.0 and pH 8.0.

The enhancement of nisin by EDTA was concentration dependent, the optimal concentration being in the range 0.3 mM to 10 mM EDTA at both pH values 5.0 and 8.0. At concentrations greater than 10 mM EDTA at pH 8.0, the activation of nisin by EDTA is reduced. However, as is shown in test #5 (Table 7), in the presence of 1.0% bovine serum albumin at pH 8.0, the efficacy of nisin towards S. typhimurium on chicken muscle is expressed throughout the range of EDTA concentrations up to 100 mM.

Thus, bactericides containing nisin and low concentrations of chelating agent, such as EDTA in the range 0.1 mM to 20 mM, can be extremely effective for the elimination or prevention of contamination of food by Gram negative bacteria.

EXAMPLE 8

Titration of Nisin Activity Against Gram Negative Bacteria (S. typhimurium)

At the optimal concentration of chelating agent, the efficacy of the bactericide in Tris buffer towards Gram negative bacteria was demonstrated to be substantial, as is shown in Table 8.

TABLE 8

| Test # | Initial Viable Bacterial Count | EDTA (mM) | BSA % | Nisin ug/ml | | | | | | | |
|---|---|---|---|---|---|---|---|---|---|---|---|
| | | | | 0 | 0.1 | 0.3 | 1.0 | 3.0 | 10 | 30 | 100 |
| | | | | % Survival at 2 hours | | | | | | | |
| 1 | 6 × 10$^6$ | 0 | 0 | 100 | — | — | — | — | 51.3 | — | 1.6 |
| 2 | 6 × 10$^6$ | 1.0 | 1.0 | 63 | 0.7 | 0.08 | 0.01 | 0.05 | 0.01 | <10$^{-4}$ | — |

In test #2 (Table 8), it can be seen that as little as 0.3 μg/ml of nisin, with 1.0 mM EDTA in 20 mM Tris at pH 8.0 in the presence of 1% bovine serum albumin (BSA), significantly reduced the survival of S. typhimurium. The bactericide is as active towards Gram negative bacteria as nisin alone is towards Gram positive Streptococci.

EXAMPLE 9

Titration of Nisin Activity Against Gram Negative Bacteria (S. typhimurium)

At the optimal concentration of chelating agent, the efficacy of a bactericide towards Gram negative bacteria in the presence of biological tissue was demonstrated with S. typhimurium on chicken muscle, and is shown in Table 9.

TABLE 9

| Test # | pH | Initial Viable Bacterial Count | EDTA (mM) | BSA (%) | Nisin μg/ml | | | | |
|---|---|---|---|---|---|---|---|---|---|
| | | | | | 0 | 10 | 100 | 200 | 300 |
| | | | | | % Survival at 2 hours | | | | |
| 1 | 8.0 | 3 × 10$^7$ | 0 | 0 | 100 | — | — | — | — |
| 2 | 8.0 | 3 × 10$^7$ | 1.0 | 1.0 | 27 | 0.26 | 0.008 | 0.007 | 0.006 |

Cubes of chicken muscle were cleansed with sodium hypochlorite and povidone iodine prior to use. To inoculate the tissue, the cubes of chicken muscle were dipped into a $10^8$ cells/ml suspension of *S. typhimurium* in 20 mM Tris HCl, pH 8.0. Excess moisture was removed from dipped cubes by tapping. The tissue was placed into sufficient buffer containing the nisin compositions to cover the tissue, and incubated for 2 hours at 37° C. after which the tissue was removed to sufficient Phage buffer to cover the tissue. The bacteria remaining in the test solution were collected by centrifugation, washed with Phage buffer, and combined with bacteria washed from the tissue by Phage buffer. The combined samples (termed "unadhered" cells) were serially diluted and 100 µl aliquots were plated for determination of surviving bacteria.

EXAMPLE 10

Nisin EDTA and Methyl Paraben Activity Against Gram Negative Bacteria (*S. typhimurium*)

A bactericide containing nisin and EDTA, when combined with a known food preservative, methyl paraben, was demonstrated to be exceptionally effective towards Gram negative bacteria, as shown in Table 10.

TABLE 10

| Test # | Initial Viable Bacteria Count | Nisin µg/ml | EDTA[b] (mM) | % Methyl Paraben | | |
|---|---|---|---|---|---|---|
| | | | | 0 | 0.1 | 1.0 |
| | | | | % Survival[c] at 2 hours | | |
| 1 | $3 \times 10^6$ | 0 | 10 | 11.8 | 1.0 | $10^{-4}$ |
| 2 | $3 \times 10^6$ | 300 | 10 | 0.03 | $<10^{-3}$ | $<10^{-4}$ |

[b]50 mM Na acetate buffer, pH 5.0
[c]Unadhered cells

Cubes of chicken muscle were cleaned with sodium hypochlorite and povidone iodine prior to use. To inoculate the tissue, the cubes of chicken muscle were dipped into a $10^8$ cells/ml suspension of *S. typhimurium* in 50 mM sodium acetate buffer, pH 5.0. Excess moisture was removed from dipped cubes by tapping. The tissue was placed into sufficient buffer containing nisin compositions to cover the tissue, and incubated for 2 hours at 37° C. after which the tissue was removed to sufficient Phage buffer to cover the tissue. The bacteria remaining in the test solution were collected by centrifugation, washed with Phage buffer, and combined with bacteria washed from the tissue by Phage buffer. The combined samples (termed "unadhered" cells) were serially diluted and 100 µl aliquots were plated for determination of surviving bacteria.

In test #1 (Table 10), methyl paraben in the presence of 10 mM EDTA was shown to be effective towards *S. typhimurium* only at a concentration of 1.0%. In test #2 (Table 10), however, in the presence of 300 µg/ml nisin, the effectiveness of methyl paraben and nisin towards *S. typhimurium* was substantially improved.

The compositions containing nisin and EDTA significantly improve the utility of the food preservative methyl paraben. Furthermore, the bactericides may lead to substantial reductions in the concentrations, or eliminate the need for these commonly recognized, though less desirable, food preservatives such as methyl paraben.

EXAMPLE 11

Nisin and Chelating Agent Activity Against Gram Positive Bacteria (*Staphylococcus aureus*)

The activation of nisin by a chelating agent is pH-dependent. The data in Table 11 confirm that at pH 5.0, nisin is somewhat more bactericidal towards *S. aureus* than is nisin at pH 8.0. At pH 5.0, EDTA does not enhance nisin activity towards *S. aureus* and at concentrations of EDTA greater than 10 mM, EDTA is inhibitory to the bactericidal activity of nisin. However, the bactericidal activity of nisin activated by EDTA at pH 8.0 is significantly greater than the bactericidal activity of nisin alone, or in combination with EDTA at pH 5.0.

TABLE 11

Influence of pH on the Effects of EDTA on Nisin Bactericidal Activity towards Staphyloccus aureus

| | Nisin | EDTA mM | | | | | | |
|---|---|---|---|---|---|---|---|---|
| pH | µg/ml | 0 | 0.1 | 0.3 | 1.0 | 3.0 | 10 | 30 | 100 |
| | | % Survival 2 hr[a] | | | | | | | |
| 8.0 | 0 | 100 | — | 100 | 81 | 100 | 100 | 100 | — |
| 8.0 | 3.0 | 7.4 | 0.03 | 0.01 | 0.2 | 0.4 | 3 | 56 | — |
| 5.0 | 0 | 100 | — | — | — | 100 | — | — | — |
| 5.0 | 3.0 | 0.6 | 1.0 | 1.3 | 1.4 | 1.8 | — | 34 | 80 |

[a]Initial viable count: $8.0 \times 10^6$ cfu/ml
Incubations were performed in 50 mM sodium acetate buffer, pH 5.0 or 20 mM Tris-HCl buffer, pH 8.0 at 37° C.

The bactericidal activity of nisin alone is reported (see Hurst) to be greatest at pH 5.0 or lower, and data presented in Table 11 support this. On the basis of this information it was believed that the bactericidal activation of nisin by EDTA towards *S. aureus* would likewise be greatest at lower pH. However, as can be seen in Table 11 and contrary to expectations (see Table 6), EDTA was not observed to enhance nisin activity towards Gram positive bacteria at pH 5.0. However, inhibition of nisin activity by high concentrations of EDTA was still observed at pH 5.0. Thus, the activation of nisin by a chelating agent occurs only within a range of chelator concentrations and, with respect to Gram positive bacteria, is dependent upon pH with the preferred pH range greater than pH 5.0.

EXAMPLE 12

Nisin and Chelating Agent Activity Against Gram Positive Bacteria

The effects of EDTA on the bactericidal activity of nisin at pH 8.0 are not limited to *S. aureus*, an important human pathogen, but are also observed with *Streptococcus mutans*, responsible for dental plaque (Table 12A), *Listeria monocytogenes*, a foodborne pathogen (Table 12B), and with a mixed population of axillary Coryneform bacteria, contributors to body odor (Table 12C).

TABLE 12A

The Effects of EDTA on the Bactericidal Activity of Nisin towards Streptococcus mutans

| | Nisin | EDTA mM | | | | | | | |
|---|---|---|---|---|---|---|---|---|---|
| pH | µg/ml | 0 | 0.01 | 0.1 | 0.3 | 1.0 | 3.0 | 10 | 30 | 100 |
| | | % Survival after 2 hr[a] | | | | | | | | |
| 8.0 | 0 | 100 | — | — | — | — | — | — | — | — |
| 8.0 | 0.1 | 4.3 | 1.8 | 0.04 | 0.02 | 0.06 | 1 | 25 | 100 | 100 |

[a]Initial viable count: $6.0 \times 10^6$ cfu/ml
Incubations were performed in 20 mM Tris-HCl, pH 8.0 at 37° C.

TABLE 12B

The Effects of EDTA on the Bactericidal Activity towards Listeria monocytogenes

| pH | Nisin µg/ml | \multicolumn{8}{c}{EDTA mM} |
|---|---|---|---|---|---|---|---|---|
| | | 0 | 0.1 | 0.3 | 1.0 | 3.0 | 10 | 30 | 100 |
| | | \multicolumn{8}{c}{% Survival after 2 hr*} |
| 8.0 | 0 | 100 | — | — | 84 | — | — | — | — |
| 8.0 | 3.0 | 0.71 | 0.04 | 0.04 | 0.02 | 0.1 | 0.64 | 10 | 14 |

*Initial viable count: $6.0 \times 10^6$ cfu/ml
Incubations were performed in 20 mM Tris-HCl, pH 8.0 at 37° C.

TABLE 12C

The Effects of EDTA on Nisin Bactericidal Activity towards Coryneform bacteria

| pH | Nisin ug/ml | \multicolumn{6}{c}{EDTA mM} |
|---|---|---|---|---|---|---|---|
| | | 0 | 0.1 | 0.3 | 1.0 | 3.0 | 10 |
| | | \multicolumn{6}{c}{% Survival 2 hr*} |
| 8.0 | 0 | 100 | — | 4.6 | 3.6 | 8 | 36 |
| 8.0 | 3 | 0.22 | 0.03 | 0.0009 | 0.1 | — | 0.16 |

*Initial viable count: $1.0 \times 10^6$ cfu/ml
Incubations were performed in 20 mM Tris-HCl, pH 8.0 at 37° C.

EXAMPLE 13

Rapid Bactericidal Activity of Nisin Activated by Chelator

The bactericide comprising nisin with EDTA is rapidly bactericidal as is illustrated by the data presented in Table 13A. Suspensions of the Gram positive bacterium *S. mutans* at $10^7$ cells/ml were incubated in 20 mM Tris buffer, pH 7.3 at 37° C. with a range of concentrations of nisin activated by 1 mM EDTA. The suspensions were incubated for various times ranging from 0.5 to 60 minutes with the bactericides. The bactericidal efficacy of the bactericides was estimated by determining the percent survival of bacteria. Enhanced by EDTA, as little as 10 µg/ml of the nisin in this formulation is able to reduce the bacterial load by 6 logs within 1 minute.

Rapid bactericidal activity is a prerequisite for effective disinfection. Thus, the compositions are predicted to be effective bactericides particularly as demonstrated here, as a component of a mouthwash, rinse, toothpaste, or other similar dentrifice active against plaque forming *S. mutans*.

The activity of nisin enhanced by EDTA against Gram negative bacteria after 2-3 hours was shown in Examples 1-7. Rapid bactericidal activity of nisin enhanced by EDTA is also seen towards Gram negative bacteria and this is illustrated by the data in Table 13B.

TABLE 13A

Kinetics of Bactericidal Activity towards *Streptococcus mutans* of Nisin Enhanced by EDTA

| Incubation Time (Minutes) | \multicolumn{6}{c}{Nisin µg/ml with 1.0 mM EDTA} |
|---|---|---|---|---|---|---|
| | 0 | 1 | 3 | 10 | 30 | 100 |
| | \multicolumn{6}{c}{% Survival*} |
| 0.5 | — | — | — | — | — | $<10^{-4}$ |
| 1 | — | — | — | $<10^{-4}$ | $<10^{-4}$ | $<10^{-4}$ |
| 3 | 100 | 0.5 | 0.002 | $<10^{-4}$ | $<10^{-4}$ | — |
| 15 | — | 0.03 | $<10^{-4}$ | $<10^{-4}$ | — | — |
| 30 | — | — | $<10^{-4}$ | — | — | — |
| 60 | 100 | 0.003 | — | — | — | — |

*Control viable cell count: $1.0 \times 10^7$ cfu/ml
Incubations were performed in 20 mM Tris-HCl, pH 7.3 at 37° C.

TABLE 13B

Rapid Bactericidal Activity towards *Escherichia coli* of Nisin Enhanced by EDTA

| mM EDTA | \multicolumn{7}{c}{Nisin ug/ml} |
|---|---|---|---|---|---|---|---|
| | 0 | 0.3 | 1.0 | 3 | 10 | 30 | 100 |
| | \multicolumn{7}{c}{% survival at 1 min*} |
| 1.0 | 100 | 100 | 56 | 0.37 | 0.013 | 0.015 | 0.008 |

*Initial viable count: $1.0 \times 10^7$ cfu/ml
Incubations were performed in 20 mM Tris, pH 7.0 at 37° C.

EXAMPLE 14

Effect of Divalent Cations on EDTA Enhancement of Nisin Activity

Divalent cations bind to EDTA and other chelating agents and would be expected to neutralize the activation of nisin by EDTA. However, as can be seen by the data in Table 14, the bactericidal activity of nisin against *S. mutans* is enhanced by 1 mM EDTA even in the presence of 1 mM $Ca^{2+}$ ion; only above 3 mM was $Ca^{2+}$ ion inhibitory to EDTA-activated nisin. This is particularly important in mouthwash applications where calcium ion concentrations are relevant.

TABLE 14

Rapid Bactericidal Activity towards *Streptococcus mutans* of Nisin Activated by EDTA in the presence of Divalent Cation

| Nisin | \multicolumn{6}{c}{$CaCl_2$ mM} |
|---|---|---|---|---|---|---|
| | 0 | 0.1 | 0.3 | 1.0 | 3 | 10 |
| | \multicolumn{6}{c}{% survival at 1 min.*} |
| 0 | 100 | | | | | |
| 3 | 2.9 | | | | | |
| 3[B] | 0.0042 | 0.0042 | | 0.052 | | 18 |
| 30[B] | 0.0019 | | 0.0003 | 0.0004 | 0.06 | 6.8 |
| 100[B] | $<10^{-4}$ | | $<10^{-4}$ | $<10^{-4}$ | 0.0001 | 1.5 |

[B]1 mM $Na_2EDTA$
*Initial viable count $1.0 \times 10^2$ cfu/ml.
Incubations performed in 10% Fetal Calf Serum at 37° C.

EXAMPLE 15

Nisin and Surfactant Activity Against Gram Positive Bacteria

The bactericidal activity of nisin can also be significantly enhanced when combined with a surfactant alone. This is best illustrated at a limiting nisin concentration (0.2 µg/ml) as shown in Table 15A. At concentrations up to 0.1%, the food grade surfactant monolaurin has little significant bactericidal activity towards *Streptococcus agalactiae* in the complex medium milk. Nisin, at concentrations up to 0.2 µg/ml, likewise does not exhibit significant bactericidal activity in milk. However, the combination of the two agents, 0.1% monolaurin and nisin 0.2 µg/ml, is extremely potent towards *S. agalactiae*. This bactericide is over 100 times more active than what would be expected for the additive effect and 10,000 times more active than either of the components individually. Thus, when the application of nisin is limited by its available activity, a bactericide comprising nisin with a surfactant can be expected to be more useful.

An example of where the application of nisin is limited by its available activity is illustrated by the data in Table 15B. Although nisin, and particularly the bactericide comprising nisin and EDTA, is bactericidal towards *L. monocytogenes*, the data in Table 15B demonstrate that in a complex medium like milk the available nisin activity towards this organism is restricted. However, the bactericide comprised of nisin with the glyceride, mono-oleate, is effective in milk towards this foodborne pathogen even though monooleate by itself had no bactericidal activity towards this organism.

TABLE 15A

Nisin Bactericidal Activity towards *Streptococcus agalactiae* in milk at 37° C.
(Activation of nisin by monolaurin)

| Nisin | Monolaurin (%) | | |
|---|---|---|---|
| (µg/ml) | 0 | 0.01 | 0.1 |
| | % survival at 2 h* | | |
| 0 | 100 | 100 | 4.5 |
| 0.02 | 100 | 100 | 0.2 |
| 0.2 | 2.2 | 0.05 | 0.0008 |

*Initial visable counts 6.0 × $10^7$ cfu/µl.
Incubations were in milk at 37° C.

TABLE 15B

Nisin Bactericidal Activity towards *Listeria monocytogenes* in milk at 37° C.
(Activation of nisin by monooleate)

| Nisin | % Monooleate | | |
|---|---|---|---|
| µg/ml | 0 | 0.1 | 1.0 |
| | % Survival 2 hr* | | |
| 0 | 100 | 67 | 63 |
| 100 | 0.56 | $10^{-3}$ | $10^{-4}$ |

*Initial viable count 5.0 × $10^7$ cfu/ml
Incubations were in milk at 37° C.

We claim:

1. A bactericidal composition comprising a lanthionine-containing bacteriocin and a chelating agent.

2. A bactericidal composition comprising a lanthionine-containing bacteriocin, a chelating agent and a surfactant.

3. The composition as defined in claim 1 or 2 wherein the lanthionine containing bacteriocin is selected from the group consisting of nisin, subtilin, epidermin, cinnamycin, duramycin, ancovenin and Pep 5.

4. The composition as defined in claim 1 or 2 wherein the chelating agent is selected from the group consisting of alkyldiamine tetraacetates, CaEDTA, $Na_2CaEDTA$, EGTA and citrate.

5. The composition as defined in claim 4 wherein the alkyldiamine tetraacetate is EDTA and the bacteriocin is nisin.

6. The composition as defined in claim 2 wherein the surfactant is selected from the group consisting of glycerides, fatty acids, emulsifiers, quaternary compounds, amphoteric surfactants and nonionic surfactants.

7. The composition as defined in claim 1 also containing a food preservative.

8. An enhanced broad range bactericide comprising a carrier, a lanthionine containing bacteriocin and a chelating agent.

9. An enhanced broad range bactericide comprising a carrier, a lanthionine containing bacteriocin, a chelating agent and a surfactant.

10. The enhanced broad range bactericide as in claim 8 or 9 wherein the lanthionine containing bacteriocin selected from the group consisting of nisin, subtilin, epidermin, cinnamycin, duramycin, ancovenin and Pep 5 and the chelating agent selected from the group consisting of alkyldiamine tetraacetates, EGTA and citrate are present in quantities such that the bactericide has enhanced effectiveness against at least one of the bacteria from the group consisting of *Staphylococcus aureus*, *Streptococcus mutans*, *Listeria monocytogenes*, *Streptococcus agalactiae*, Cornyeform bacteria, *Salmonella typhimurium*, *Escherichia coli*, *Klebsiella pneumoniae*, *Pseudomonas aeruginosa*, *Bacterioides gingivalis* and *Actinobacillus actinomycetescomitans*.

11. The enhanced broad range bactericide as in claim 10 wherein the alkyldiamine tetraacetate is EDTA.

12. The enhanced broad range bactericide as in claim 10 wherein the concentration of nisin is between about 0.1 µg/ml and 300.0 µg/ml and the concentration of chelating agent is between about 0.1 mM and 20 mM.

13. The enhanced broad range bactericide as in claim 9 wherein the surfactant is selected from the group consisting of glycerides, fatty acids, quaternary compounds, emulsifiers, amphoteric surfactants and nonionic surfactants and is present in an amount sufficient such that the bactericide has enhanced effectiveness against at least one of the bacteria from the group consisting of Gram negative and Gram positive bacteria.

14. The enhanced broad range bactericide as in claim 13 wherein the concentration of surfactant is between about 0.01% and 1.0%.

* * * * *